United States Patent [19]

Teves

[11] Patent Number: 4,721,506
[45] Date of Patent: Jan. 26, 1988

[54] FLAT-INCLINED TIP NEEDLE

[76] Inventor: Leonides Y. Teves, 623 - 39th St. West, Bradenton, Fla. 33505

[21] Appl. No.: 928,187

[22] Filed: Nov. 7, 1986

[51] Int. Cl.$^4$ ............................................. A61M 31/00
[52] U.S. Cl. ....................................... 604/51; 604/158; 604/164; 604/170
[58] Field of Search ................. 604/51, 158, 164, 165, 604/170, 272, 273, 274; 128/753, 754

[56] References Cited

U.S. PATENT DOCUMENTS

| | | | |
|---|---|---|---|
| 1,527,291 | 2/1925 | Zorraquin | 604/158 |
| 2,922,420 | 1/1960 | Cheng | 604/158 X |
| 4,645,491 | 2/1987 | Evans | 604/273 X |
| 4,650,472 | 3/1987 | Bates | 604/170 X |

*Primary Examiner*—John D. Yasko
*Attorney, Agent, or Firm*—Frijouf, Rust & Pyle

[57] ABSTRACT

An epidural needle and method of use are disclosed involving a needle shaft having a first end and a second end with an axial channel extending therebetween. The first end of the needle shaft includes an inclined surface and a rounded and blunted point. The second end of the needle includes an attachment means. A solid rod having an inclined surface and a rounded and blunted point is receivable into the axial channel of the needle shaft. When the solid rod is positioned within the axial channel of the needle shaft, the point of the solid rod and the needle together form a unitary tip having an inclined portion and a blunted portion. The blunted portion forms an end face disposed at an angle of about 80 to 100 degrees relative a longitudinal axis of the needle. The unitary tip avoids nicking, piercing, severing, or perforating the veins, arteries, nerves and dura of the patient in traversing the spinal ligaments and in entering a space proximate the dura matter of a spinal cord of a patient to provide liquid communication with the space when the solid rod is withdrawn from the axial channel of the needle.

7 Claims, 7 Drawing Figures

FLAT-INCLINED TIP NEEDLE

BACKGROUND OF THE INVENTION

1. Field of the Invention

This invention relates to an improved needle for the administration of an anaesthetic agent within the epidural space, and more particularly to a needle tip which minimizes injury to the veins, arteries, nerves and dura of a patient when traversing an area proximate spinal ligaments, such as the ligamentum flavum, to enter a space proximate the dura mater of spinal cord of a patient.

2. Information disclosure statement

Numerous needles are presently in use for effecting an epidural administration of an anaesthetic agent to produce anesthesia. The major disadvantage is the possible penetration of the dura which may result in a severe headache to the recipient-patient.

U.S. Pat. No. 3,782,381 describes a precurved, over the needle catheter with a wing assembly to aid in proper securement of the catheter at the site of the tissue puncture.

U.S. Pat. No. 4,349,023 discloses a device which minimizes kinking of a tubing being inserted through a needle into the eqidural space of a patient.

U.S. Pat. No. 4,518,383 discloses an instrument for eqidural and spinal anesthesia which has an outer assembly and inner assembly. The outer assembly is bent at an angle of about 20° and has an inclined, pointed tip that makes an angle of about 10° with the axis of the instrument. The inner assembly is a hollow needle which extends within the needle of the outer assembly and projects into its forward end. The inner needle also has an inclined, pointed tip that makes an angle of about 30° with the axis of the instrument.

U.S. Pat. No. 4,543,092 discloses a catheter set where the tip of the mandrin includes side facets which are advantageously ground on opposite sides of the tip of the mandrin in order to reduce the wall thickness of the mandrin and the angle of the tip of the mandrin is between 35 and 45 degrees relative the axis of the mandrin.

These devises, however, utilize a sharp needle tip which fails to minimize the damage to the nerves and blood vessels.

U.S. Pat. No. 2,922,420 discloses a blunted epidural needle which utilizes a lateral opening at the tip end.

Epidural anaesthesia is accomplished by using an epidural needle to enter the epidural space. After entering the epidural space the dura mater is encountered. Care must be taken not to penetrate the dura. In the event the dura is penetrated, adverse results, such as a severe headache may occur.

Therefore, it is an object of this invention to provide an epidural needle device which minimizes the damage to the nerves and/or blood vessels through the use of a flat tipped and inclined needle point when entering the epidural space or the space outside the dura mater of the spinal cord thereby increasing the safety of epidural administration while providing for prompt and rapid penetration into the epidural space.

It is a further object of this invention to provide an epidural needle device which does not require a catheter to be inserted into the passageway of the needle to administer a drug into the epidural space.

It is a further object of this invention to provide a needle which injects an anesthetic, or the like, straight from the tip of the needle thereby minimizing loss of anesthetic to surrounding tissue.

It is a further object of this invention to provide an epidural needle device which utilizes a small gauge needle shaft to limit the damage caused by the insertion of the needle device.

It is a further object of this invention to provide a unitary tip which comprises a needle shaft having an axial channel and a solid rod being received into the axial channel such that the tip of the needle and the tip of the solid rod together form a unitary tip which aids in traversing the tissue of a patient.

It is a further object of this invention to provide an epidural needle device which does not require special insertion apparatus.

It is a further object of the invention to provide a needle tip which easily traverses the spinal ligaments to arrive at the epidural space and which minimizes or prevents penetration of the dura and possible further penetration into the subarachnold space which minimizes or prevents the occurance of a headache resulting from penetration of the dura.

The foregoing has outlined some of the more pertinent objects of the present invention. These objects should be construed to be merely illustrative of some of the more pertinent features and applications of the invention. Many other beneficial results can be obtained by applying the disclosed invention in a different manner or modifying the invention within the scope of the disclosure. Accordingly, other objects and a fuller understanding of the invention may be had by referring to the summary of the invention and the detailed description describing the preferred embodiment in addition to the scope of the invention defined by the claims taken in conjunction with the accompanying drawings.

SUMMARY OF THE INVENTION

The needle of the present invention is defined by the appended claims with a specific embodiment shown in the attached drawings. For the purpose of summarizing the invention, the invention relates to an epidural needle for use with a syringe for administrating a liquid injection to a space proximate the dura mater of a spinal cord of a patient comprising a needle shaft having a first end and a second end with an axial channel extending therebetween. The second end of the needle shaft includes an attachment means for providing a liquid tight engagement with the syringe. The first end of the needle shaft includes an inclined surface and a rounded and blunted point. A solid rod with a first end and a second end is utilized. The first end of the solid rod includes an inclined surface and a rounded and blunted point which is slidably receivable into the axial channel of the needle shaft such that the first end of the solid rod is aligned with the first end of the needle shaft in a close fitting manner. The point of the needle shaft and the point of the solid rod when positioned in the axial channel of the needle shaft together define a unitary tip configuration. The unitary tip configuration includes a smooth junction of the first end of the needle shaft and the first end of the rod and forms a tip having a blunt portion and an inclined portion. The blunt portion of the tip forms an end face disposed at an angle of about 80° to 100° relative a longitudinal axis of the needle shaft. The unitary tip avoids nicking, piercing, severing, or perforating the veins, arteries, nerves and dura of the patient when the needle of the invention traverses the spinal ligaments, such as the ligamentum flava, and enters a space proximate the dura mater of a spinal cord of a patient. The needle provides liquid communication with the space when the solid rod is withdrawn from the axial channel of the needle shaft to enable the prescribed injection to be introduced into the space by a syringe. The invention also relates to a method of use of the epidural needle.

In a further embodiment of the epidural needle, the blunt portion of the unitary tip forms an end face disposed at an angle of about 90° relative a longitudinal axis of the needle shaft.

In a further embodiment of the epidural needle the inclined portion of the tip is inclined at an angle of about 40° to 50° relative the longitudinal axis of the needle.

In a preferred embodiment the inclined portion of the unitary tip is inclined at about an angle of about 45° relative the longitudinal axis of the needle.

In another embodiment the attachment means includes a hub which sealingly engages a syringe tip thereby providing for the attachment of a conventional syringe for direct injection of the epidural anesthestic into the space proximate the dura mater of the spinal cord of a patient.

The most preferred embodiment of the invention comprises a needle shaft having an axial channel extending therethrough. The needle shaft includes a first end and a second end with the second end of the needle shaft having a hub for providing a liquid tight engagement with a syringe and the first end of the needle having an inclined surface and a rounded and blunted point. A solid rod having a first end and a second end is slidably receivable into the axial channel of the needle shaft in a close fitting relation. The first end of the solid rod includes an inclined surface and a rounded and blunted point. The point of the needle shaft and the point of the solid rod, when positioned within the axial channel of the needle shaft with the first end of the needle shaft aligned with the first end of the rod, together define a unitary tip configuration. This tip configuration includes a smooth junction between the first end of the needle shaft and the first end of the rod to form a tip with a blunt portion and an inclined portion. The inclined portion of the unitary tip is inclined at an angle of about 40° to 50° relative a longitudinal axis of the needle and comprises about 70% of the diameter of the needle. The blunt portion of the unitary tip forms an end face disposed at an angle of about 90° relative the longitudinal axis of the needle shaft and comprises about 30% of the diameter of the needle whereby the unitary tip avoids nicking, piercing, severing, or perforating the veins, arteries, nerves and dura of the patient in traversing the ligamentum flavum and in entering a space proximate the dura mater of the spinal cord of the patient to provide liquid communication with the space when the solid rod is withdrawn from the axial channel of the needle shaft. The prescribed injection may then be introduced to the space proximate the dura mater of a spinal cord of the patient by the syringe, or a portion of spinal fluid may then be removed from this space.

A method of effecting liquid communication with an epidural space of a patient is disclosed by providing an epidural needle for use with an introducer, stylet and a syringe. The epidural needle comprises a needle shaft having a first and second end with an axial channel extending therebetween. The second end of the needle shaft includes an attachment means to enable liquid tight engagement with the syringe. The first end of the needle shaft includes an inclined surface and a rounded and blunted point. A solid rod with a first end and a second end is slidably receivable into the axial channel of the needle shaft in a close fitting relation. The first end of the solid rod further includes an inclined surface and a rounded and blunted point. The point of the needle shaft and the point of the solid rod together define a unitary tip configuration when positioned in the axial channel of the needle shaft such that the first end of the needle shaft is aligned with the first end of the solid rod. A smooth junction between the first end of the needle shaft and the first end of the rod forms a unitary tip having a blunt portion and an inclined portion. The blunt portion of the tip forms an end face disposed at an angle of about 80° to 100° relative a longitudinal axis of the needle shaft.

An epidural injection is conducted by puncturing the skin and flesh of a patient up to the spinal ligaments, such as the ligamentum flavum which connects the lamina of the adjacent vertebrae, with an introducer comprising a needle with a sharp tip and having a first and second end with an axial channel extending therethrough. Optionally, a stylet may be inserted into the axial channel of the introducer prior to inserting the introducer into the skin and flesh. The introducer is pushed through the tissue until an increased resistance is ascertained indicating penetration to an area proximate the spinal ligaments. If used, the stylet is then removed from the axial channel of the introducer. The needle of the invention is inserted, with the solid rod disposed therein, into the axial channel of the introducer. The epidural needle is pushed through the spinal ligaments and into the epidural space whereby the unitary tip avoids nicking, piercing, severing, and perforating the veins, arteries, nerves and dura of the patient in traversing the spinal ligaments and in entering a space proximate the dura mater of spinal cord of a patient to provide liquid communication with the space. The solid rod then is withdrawn from the epidural needle thereby providing liquid communication with the space via the axial channel of the epidural needle shaft. A syringe is connected to the attachment means of the epidural needle to enable the administration of an anesthetic agent, X-ray contrasting agent or the like via the needle into the epidural space.

The foregoing has outlined rather broadly the more pertinent and important features of the present invention in order that the detailed description of the invention that follows may be better understood so that the present contribution to the art can be more fully appreciated. Additional features of the invention will be described hereinafter which form the subject of the claims of the invention. It should be appreciated by those skilled in the art that the conception and the specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should be had to the following detailed description taken in connection with the accompanying drawings in which.

Similar reference characters refer to similar parts throughout the several views of the drawings.

DETAILED DESCRIPTION OF THE DRAWINGS

Figure 1:
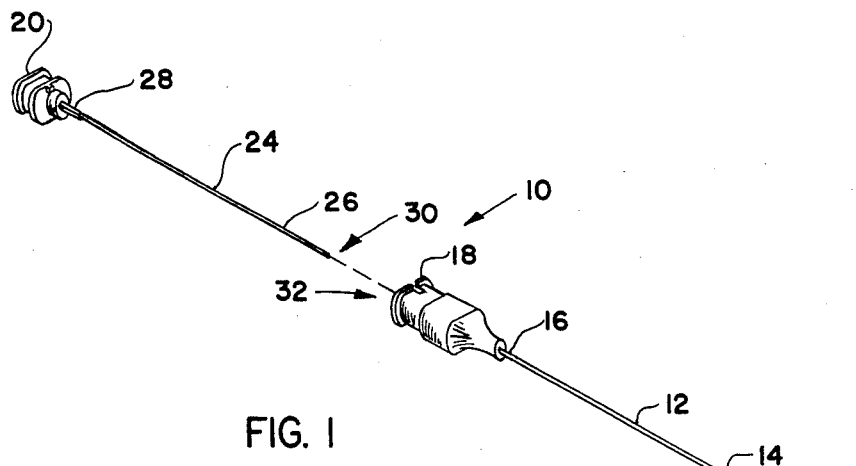
FIG. 1 illustrates an exploded isometric view of the epidural needle.

FIG. 1 illustrates an isometric view of the epidural needle 10 having a needle shaft 12 with a first end 14 and a second end 16 and with an attachment means 18 to enable liquid tight engagement with a syringe (not shown). The attachment means 18 illustrated at FIG. 1 may be a Leur assembly for use with, for example, a Leur-Lok syringe. The first end 14 of the needle shaft 12 includes an inclined surface and a rounded and blunted point 22. A solid rod 24 having a first end 26 and a second end 28 is illustrated. The first end 26 of solid rod 24 defines an inclined surface and a rounded and blunted point 30. The solid rod 24 is positioned along an axis of the axial channel 32 of the needle shaft 12 prior to being received by the axial channel 32. The first end 26 of solid rod 24 is slidably receivable into the axial channel 32 (indicated generally in FIG. 2) of the needle shaft 12 in a close fitting relation. Solid rod 24 is positioned within the passageway or axial channel 32 of needle shaft 12 during penetration of the tissue of a patient in order to prevent the body tissue from blocking axial channel 32. The point 22 of the needle shaft 12 and the point 30 of the solid rod 24 together define a unitary tip configuration when the solid rod 24 is positioned in the axial channel 32 of the needle shaft 12 and the first end 14 of the needle shaft 12 is aligned with the first end 26 of the solid rod 24. A smooth junction between the first end 14 of the needle shaft 12 and the first end 26 of the rod 24 forms a blunted and inclined unitary tip configuration 38 having a blunt portion 42 and an inclined portion 44 (preferably substantially planar) as illustrated generally at FIG. 2. The blunt portion 42 of the unitary tip configuration 38 forms an end face 42 disposed at an angle A of about 80° to 100° relative a longitudinal axis AX of the needle shaft 12 as illustrated at FIG. 3.

A grasping means 20 for grasping the second end 28 of solid rod 24 permits the solid rod 24 to be easily positioned, inserted and withdrawn from the axial channel 32.

Figure 2:
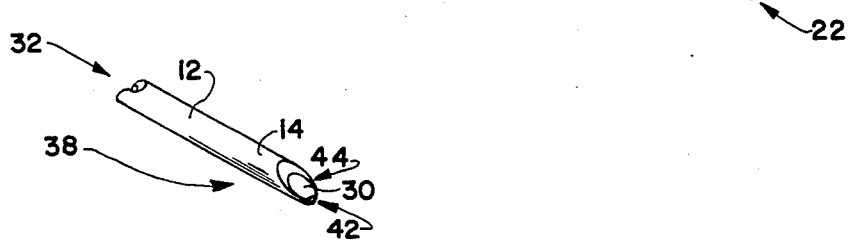
FIG. 2 illustrates an isometric view of the epidural needle tip.

FIG. 2 illustrates an isometric view of the epidural needle unitary tip 38 with the first end 14 needle shaft 12 and the first end 26 of solid rod 24 within the axial channel 32 of the needle shaft 12 in a close fitting relation. The first end 14 of the needle shaft 12 and the first end 26 of the solid rod 24 define a inclined, rounded and blunted unitary tip configuration 38. The point 22 of the needle shaft 12 and the point 30 of the solid rod 24 together define a unitary tip configuration 38 when the first end 26 of the solid rod 24 is aligned within the axial channel 32 with the first end 14 of the needle shaft 12, as illustrated at FIG. 2. A smooth, combination tip is formed by the inclined surfaces and rounded and blunted points 22 and 30 which together define unitary tip configuration 38 having a blunt portion 42 and an inclined portion 44. The blunt portion 42 of the tip configuration 38 forms an end face disposed at an angle A of about 80° to 100° relative a longitudinal axis AX of the needle shaft 12.

Figure 3:
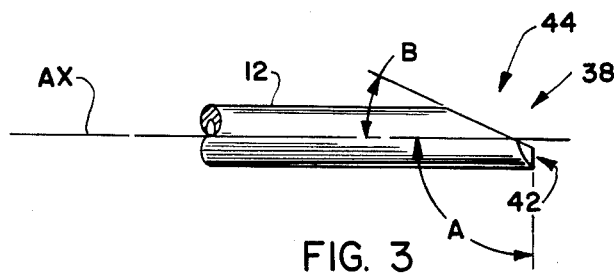
FIG. 3 illustrates a right side view of the epidural needle tip.

FIG. 3 illustrates a right side view of the epidural needle tip 38 with the inclined portion 44 and the blunt portion 42. The blunted porton 42 comprises about 30% of the diameter of the needle 10 and forms an angle A of about 90° relative the longitudinal axis AX. The wedge-shaped or inclined portion 44 of the unitary tip 38 forms an angle B of about 45° relative the longitudinal axis AX.

Figure 4:
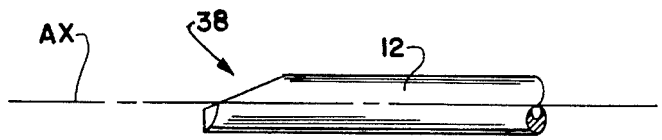
FIG. 4 illustrates a left side view of the epidural needle tip.

FIG. 4 illustrates a left side view of the epidural needle tip 38 which is the mirror image of FIG. 3. FIG. 4 illustrates the symmetry of needle point sides.

Figure 5:
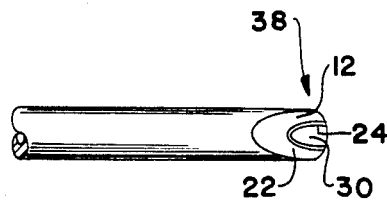
FIG. 5 illustrates a top view of the epidural needle tip.

FIG. 5 illustrates a top view of the epidural needle tip 38 showing the rounded and blunted tips 22 and 30 of the needle shaft 12 and the solid rod 24, respectively.

Figure 6:
FIG. 6 illustrates a bottom view of the epidural needle tip.

FIG. 6 illustrates a bottom view of the epidural needle tip 38 which shows the smooth and rounded first end 14 of the needle shaft 12.

Figure 7:
FIG. 7 illustrates a top view of the epidural needle tip absent the solid rod.

FIG. 7 illustrates a top view of the epidural needle tip 38 absent the solid rod 24. The axial channel 32 extends axially through the needle shaft 12 to form a passage for the solid rod (not shown) to be received. The channel 32 also provides a conduit through which an epidural anesthetic or the like is carried to the epidural space after the unitary tip 38 is located thereat.

The needle of the invention is manufactured by grinding a conventional needle for injection of sufficient length for an epidural injection, preferably a needle having a needle shaft of approximately, 22 gauge, with the solid rod positioned within the channel of the needle shaft such that the first end 26 of the solid rod 24 is aligned within the axial channel 32 with the first end 14 of the needle shaft 12. This insures that both the first end 14 of the needle shaft 12 (containing point 22) and the first end 26 of the solid rod 24 (containing point 30) are ground simultaneously and together resulting in a smooth, rounded, blunted end face with a smooth incline to define a unitary tip configuration 38. The blunted surface of the needle tip 38 must be completely rounded, as illustrated at FIGS. 5-7, to insure that during penetration the needle tip minimizes tissue injury. Generally, it follows that the smaller the diameter of the needle shaft, the less chance of tissue injury.

The axial channel or bore 32 of the needle shaft 12 is dimensioned to receive the rod 24 in a close fitting manner in order to prevent tissue from entering the circumferential area of the axial channel not occupied by the diameter of the solid rod 24. It is believed that the inclined portion 44 of the epidural tip 38 forms a wedge to aid in the transversal of the spinal ligaments while the blunted portion 42 acts as a plow, pushing the veins, arteries and nerves away from the path being traversed. This is, however merely a theoretical explanation at this point and the inventor does not consider himself bound by it as the only explanation.

In using the epidural needle of the invention the skin is first sterilized by the use of alcohol or the like. A local anesthetic is injected into the skin tissue proximate the position of the intended epidural injection. An introducer, optionally with a stylet, well known to those skilled in the art, is pushed through the skin and flesh of a patient up to an area proximate the spinal ligaments indicated by an ascertainment of an increased resistance. If used, the stylet is then removed from the axial channel of the introducer. The epidural needle with the solid rod disposed therein, is positioned into the axial channel of the introducer. The epidural needle is pushed through the spinal ligaments and into the epidural space whereby the unitary tip avoids nicking, piercing, severing, and perforating the veins, arteries, nerves and dura of the patient in traversing the ligamentum flavum and entering a space proximate the dura mater of spinal cord of a patient to provide liquid communication with the space. The solid rod is withdrawn from the epidural needle and a syringe connected to the attachment means of the epidural needle to provide liquid communication with the space via the axial channel of the epidural needle to enable the administration of an anesthetic agent, or the like, via the needle into the epidural space.

Entry into the epidural space is ascertained by any of a number of methods known to those skilled in the art. For example, the hanging drop method which takes advantage of the negative pressure which exists in the epidural space indicates entry into the epidural space by the movement of the hanging drop into the needle. Also, a sharp decrease in resistance pressure when pushing the needle toward the epidural space indicate entry into the epidural space.

The present disclosure includes that contained in the appended claims as well as that of the foregoing description. Although this invention has been described in its preferred form with a certain degree of particularity. It is understood that the present disclosure of the preferred form has been made only by way of example and that numerous changes in the details of construction and the combination and arrangement of parts may be resorted to without departing from the spirit and scope of the invention.

What is claimed is:

1. An epidural needle for providing liquid communication with a space proximate the dura mater of a spinal cord of a patient comprising:
    a needle shaft having a first end and a second end with an axial channel extending therebetween;
    said second end of said needle shaft having an attachment means for providing a liquid tight engagement with the syringe;
    said first end of said needle shaft having an inclined surface and a rounded and blunted point;
    a solid rod having a first end and a second end and being slidably receivable into said axial channel of said needle shaft such that said first end of said solid rod is aligned with said first end of said needle shaft;
    said first end of said solid rod having an inclined surface and a rounded and blunted point;
    said point of said needle shaft and said point of said solid rod together defining a unitary tip configuration having a blunt portion and an inclined portion;
    said blunt portion of said unitary tip forming an end face disposed at an angle of about 80° to 100° relative a longitudinal axis of said needle shaft whereby said unitary tip avoids nicking, piercing, severing, or perforating the veins, arteries, nerves and dura of the patient in traversing the spinal ligaments in and entering a space proximate the dura mater of the spinal cord of the patient to provide liquid communication with the space when the solid rod is withdrawn from the axial channel of the needle shaft.

2. The epidural needle of claim 1 wherein said end face of said blunt portion of said tip forms an end face disposed at an angle of about 90° relative said longitudinal axis of said needle shaft.

3. The epidural needle of claim 1 wherein said inclined portion of said tip is inclined at an angle of 40° to 50° relative said longitudinal axis of said needle.

4. The epidural needle of claim 1 wherein said blunted portion of said tip comprises about 30% of the diameter of the needle and forms an angle of about 90° relative said longitudinal axis.

5. The epidural needle of claim 1 wherein said attachment means is a hub.

6. An epidural needle for use with a syringe for administrating a liquid injection to a space proximate the dura mater of a spinal cord of a patient comprising:
    a needle shaft having an axial channel extending therethrough and including a first end and a second end;
    said second end of said needle shaft having a hub to enable liquid tight engagement with the syringe;
    said first end of said needle shaft having an inclined surface and a rounded and blunted point;
    a solid rod having a first end and a second end and being receivable into said axial channel of said needle shaft in a close fitting relation such that said first end of said solid rod is aligned with said first end of said needle shaft;
    said first end of said solid rod having an inclined surface and a rounded and blunted point;
    said point of said needle shaft and said point of said solid rod together defining a unitary tip configuration having a blunt portion and an inclined portion;
    said inclined portion of said tip being inclined at an angle of 40° to 50° relative a longitudinal axis of said needle such that the inclined portion comprises about 70% of the diameter of the needle; and
    said blunt portion of said tip forming an end face disposed at an angle of about 90° relative said longitudinal axis of said needle shaft such that the blunt portion comprises about 30% of the diameter of the needle whereby said tip avoids nicking, piercing, severing, or perforating the veins, arteries, nerves and dura of the patient in traversing the spinal ligaments in entering a space proximate the dura mater of the spinal cord of the patient to provide liquid communication with the space when the solid rod is withdrawn from the axial channel of the needle shaft.

7. A method of effecting liquid communication with an epidural space of a patient comprising:
    providing an epidural needle including a needle shaft having a first end and a second end with an axial channel extending therebetween and with the first end having an inclined surface and rounded and blunted point and the second end of the needle shaft having an attachment means for providing a liquid tight engagement with a syringe; a solid rod having a first end with an inclined surface and a rounded and blunted point and a second end, with the solid rod being slidably receivable into the axial channel of the needle shaft such that the first end of the solid rod is alignable with the first end of the needle shaft to define a unitary tip configuration having a blunt portion and an inclined portion comprising the point of the needle shaft and the point of the solid shaft where the blunt portion of the tip forms an end face disposed at an angle of about 80° to 100° relative a longitudinal axis of the needle shaft; and conducting an epidural injection comprising:

inserting an introducer comprising a needle with a sharp tip and having an axial channel therein through the skin and flesh of a patient up to a position proximate the spinal ligaments ascertainable by an increased penetration resistance;

inserting the epidural needle with the solid rod disposed therein, into the axial channel of the introducer;

inserting the epidural needle through the spinal ligaments and into the epidural space whereby the unitary tip avoids nicking, piercing, severing, or perforating the veins, arteries, nerves and dura of the patient in traversing the spinal ligaments and in entering a space proximate the dura mater of the spinal cord of the patient; and withdrawing the solid rod from the introducer and epidural needle to provide liquid communication with the space via the axial channel of the epidural needle.

* * * * *